United States Patent
Ruchti et al.

(10) Patent No.: US 7,640,140 B2
(45) Date of Patent: Dec. 29, 2009

(54) METHOD OF PROCESSING NONINVASIVE SPECTRA

(75) Inventors: Timothy L. Ruchti, Gilbert, AZ (US);
Thomas B. Blank, Gilbert, AZ (US);
Alexander D. Lorenz, Chandler, AZ (US)

(73) Assignee: Sensys Medical, Inc., Chandler, AZ (US)

( * ) Notice: Subject to any disclaimer, the term of this patent is extended or adjusted under 35 U.S.C. 154(b) by 852 days.

(21) Appl. No.: 11/095,331

(22) Filed: Mar. 30, 2005

(65) Prior Publication Data

US 2005/0240090 A1  Oct. 27, 2005

Related U.S. Application Data

(60) Provisional application No. 60/558,610, filed on Mar. 31, 2004.

(51) Int. Cl.
*G06F 19/00* (2006.01)
*A61B 5/00* (2006.01)

(52) U.S. Cl. .................. 702/189; 600/316
(58) Field of Classification Search ............ 702/19, 702/189; 600/316, 317, 332
See application file for complete search history.

(56) References Cited

U.S. PATENT DOCUMENTS

| | | | | |
|---|---|---|---|---|
| 6,115,673 A | * | 9/2000 | Malin et al. | 702/23 |
| 6,876,931 B2 | * | 4/2005 | Lorenz et al. | 702/22 |
| 2003/0216627 A1 | * | 11/2003 | Lorenz et al. | 600/322 |

\* cited by examiner

*Primary Examiner*—Bryan Bui
(74) *Attorney, Agent, or Firm*—Michael A. Glenn; Glenn Patent Group (57) ABSTRACT

This invention provides a method and apparatus that corrects for tissue related interference calibration and/or measurement of biological parameters noninvasively. The invention concerns such terms as outlier identification, filtering, spectral correction, and baseline subtraction steps that, when used together, provides for noninvasive measurement of biological parameters, such as glucose concentration.

14 Claims, 2 Drawing Sheets

METHOD OF PROCESSING NONINVASIVE SPECTRA

CROSS REFERENCE TO RELATED APPLICATIONS

This application claims benefit of U.S. provisional patent application Ser. No. 60/558,610 filed Mar. 31, 2004 which is incorporated herein in its entirety by this reference thereto.

BACKGROUND OF THE INVENTION

1. Field of the Invention

This invention relates generally to spectroscopic data processing technology and its application in calibration and noninvasive measurement of blood and/or tissue constituent properties, such as glucose concentration. More particularly, a method and apparatus are disclosed that use near-infrared light to detect and quantify physiological and chemical properties of an irradiated tissue sample. Still more particularly, this invention relates to a series of steps for processing noninvasive spectra using extraction of net analyte signal and/or interference removal to correct near-infrared spectra that are obscured, distorted, and/or corrupted as a result of sample heterogeneity, the dynamic nature of skin, and the chemical composition of the sampled tissue.

2. Background Discussion of the Prior Art

Diabetes

Diabetes is a leading cause of death and disability worldwide that afflicts an estimated 16 million Americans. Complications of diabetes include heart and kidney disease, blindness, nerve damage, and high blood pressure with the estimated total cost to the United States economy alone exceeding $90 billion per year, (*Diabetes Statistics*, National Institutes of Health, Publication No. 98-3926, Bethesda, Md. (November 1997); JAMA, vol. 290, pp. 1884-1890 (2003)). Long-term clinical studies show that the onset of complications are significantly reduced through proper control of blood glucose concentrations, (The Diabetes Control and Complications Trial Research Group, *The effect of intensive treatment of diabetes on the development and progression of long-term complications in insulin-dependent diabetes mellitus*, N. Eng. J. of Med., vol. 329, pp. 977-86 (1993); U.K. Prospective Diabetes Study (UKPDS) Group, *Intensive blood-glucose control with sulphonylureas or insulin compared with conventional treatment and risk of complications in patients with type 2 diabetes*, Lancet, vol. 352, pp. 837-853 (1998); and Y. Ohkubo, H. Kishikawa, E. Araki, T. Miyata, S. Isami, S. Motoyoshi, Y. Kojima, N. Furuyoshi, M. Shichizi, *Intensive insulin therapy prevents the progression of diabetic microvascular complications in Japanese patients with non-insulin-dependent diabetes mellitus: a randomized prospective 6-year study*, Diabetes Res. Clin. Pract., vol. 28, pp. 103-117 (1995)).

A vital element of diabetes management is the self-monitoring of blood glucose concentrations by diabetics in the home environment. Unfortunately, current monitoring techniques discourage regular use due to the inconvenient and painful nature of drawing blood through the skin prior to analysis. Therefore, new methods for self-monitoring of blood glucose concentrations are required to improve the prospects for more rigorous control of blood glucose concentration in diabetic patients.

Numerous approaches have been explored for measuring blood glucose concentrations ranging from invasive methods, such as microdialysis, to noninvasive technologies that rely on spectroscopy. Each method has associated advantages and disadvantages, but only a few have received approval from certifying agencies. Unfortunately, noninvasive techniques for the self-monitoring of blood glucose have not yet been certified.

Noninvasive Glucose Concentration Estimation

One method, near-infrared spectroscopy involves the illumination of a spot on the body with near-infrared electromagnetic radiation, such as light in the wavelength range about 750 to 2500 nm. The light is partially absorbed and scattered, according to its interaction with the constituents of the tissue prior to being reflected back to a detector. The detected light contains quantitative information that is based on the known interaction of the incident light with components of the body tissue, such as water, fat, protein, and glucose.

Previously reported methods for the noninvasive measurement of glucose concentration through near-infrared spectroscopy rely on the detection of the magnitude of light attenuation caused by the absorption signature of blood glucose, as represented in the targeted tissue volume. The tissue volume is the portion of irradiated tissue from which light is reflected or transmitted to the spectrometer detection system. The signal due to the absorption of glucose is extracted from the spectral measurement through various methods of signal processing and one or more mathematical models. The models are developed through the process of calibration on the basis of an exemplary calibration set of spectral measurements and associated reference blood glucose concentrations, such as fingertip, venous, or alternative site blood.

There are a number of reports on noninvasive glucose concentration estimation technologies. Some of these relate to general instrumentation configurations required for noninvasive glucose concentration determination, while others refer to sampling and processing technologies. Those related to the invention are briefly reviewed here:

Near-infrared spectroscopy has been demonstrated in specific studies to represent a feasible and promising approach to the noninvasive prediction of blood glucose concentrations. M. Robinson, R. Eaton, D. Haaland, G. Keep, E. Thomas, B. Stalled, P. Robinson, *Noninvasive glucose monitoring in diabetic patients: A preliminary evaluation*, Clin. Chem., vol. 38. pp. 1618-22 (1992) describe three different instrument configurations for measuring diffuse transmittance through the finger in the 600 to 1300 nm range. Meal tolerance tests were used to perturb the glucose concentrations of three subjects and calibration models were constructed specific to each subject on single days and tested through cross-validation. Absolute average prediction errors ranged from 19.8 to 37.8 mg/dL.

H. Heise, R. Marbach, T. Koschinsky, F. Gries, *Noninvasive blood glucose sensors based on near-infrared spectroscopy*, Artif. Org. vol. 18. pp. 439-47 (1994) and R. Marbach, T. Koschinsky, F. Gries, H. Heise *Noninvasive glucose assay by near-infrared diffuse reflectance spectroscopy of the human inner lip*, Appl. Spect. vol. 47, pp. 875-81 (1992) describe a diffuse reflectance measurement of the oral mucosa in the 1111 to 1835 nm range with an optimized diffuse reflectance accessory. In-vivo experiments were conducted on single diabetic subjects using glucose tolerance tests and on a population of 133 different subjects. The best standard error of prediction reported was 43 mg/dL, which was obtained from a two-day single person oral glucose tolerance test that was evaluated through cross-validation.

K. Jagemann, C. Fischbacker, K. Danzer K, U. Muller, B. Mertes *Application of near-infrared spectroscopy for noninvasive determination of blood/tissue glucose using neural* network, Z. Phys. Chem., vol. 191S, pp. 179-190 (1995); C. Fischbacher, K. Jagemann, K. Danzer, U. Muller, L. Papenkrodt, J. Schuler *Enhancing calibration models for noninvasive near-infrared spectroscopic blood glucose determinations*, Fresenius J. Anal. Chem., vol. 359, pp.78-82 (1997); K. Danzer, C. Fischbacher, K. Jagemann *Near-infrared diffuse reflection spectroscopy for noninvasive blood-glucose monitoring*, LEOS Newsletter, vol. 12(2), pp. 9-11 (1998); and U. Muller, B. Mertes, C. Fischbacher, K. Jagemann, K. Danzer *Noninvasive blood glucose monitoring by means of new infrared spectroscopic methods for improving the reliability of the calibration models*, Int. J. Artif. Organs, vol. 20, pp. 285-290 (1997) describe diffuse reflectance spectra over the 800 to 1350 nm range on the middle finger of the right hand with a fiber-optic probe. Each experiment involved a diabetic subject and was conducted over a single day with perturbation of blood glucose concentrations through carbohydrate loading. Results, using both partial least squares regression and radial basis function neural networks were evaluated on single subjects over single days through cross-validation. Danzer, supra, reports an average root mean square prediction error of 36 mg/dL through cross-validation over 31 glucose profiles.

J. Burmeister, M. Arnold, G. Small *Human noninvasive measurement of glucose using near infrared spectroscopy* [abstract], Pittsburgh Conference, New Orleans, La. (1998) describe absorbance spectra, collected in transmission mode, of the tongue in the 1429 to 2000 nm range. A study of five diabetic subjects was conducted over a 39-day period with five samples taken per day. Every fifth sample was used for an independent test set and the standard error of prediction for all subjects was greater than 54 mg/dL.

T. Blank, T. Ruchti, S. Malin, S. Monfre, *The use of near-infrared diffuse reflectance for the noninvasive prediction of blood glucose*, IEEE Lasers and electro-optics society newsletter, vol. 13, no. 5 (October 1999) describe the noninvasive measurement of blood glucose concentration during modified oral glucose tolerance tests over a short time period. The calibration was customized for an individual and tested over a relatively short time period.

In all of these studies, limitations were cited that affect the acceptance of such a method as a commercial product. These limitations included sensitivity, sampling problems, time lag, calibration bias, long-term reproducibility, and instrument noise. Fundamentally, however, accurate noninvasive estimation of blood glucose concentration is presently limited by the available near-infrared technology, the trace concentration of glucose relative to other constituents, and the dynamic nature of the skin and living tissue of the patient (O. Khalil *Spectroscopic and clinical aspects of noninvasive glucose measurements*, Clin. Chem., vol. 45, pp. 165-77 (1999)).

S. Malin, T. Ruchti, An intelligent system for noninvasive blood analyte prediction, U.S. Pat. No. 6,280,381 (Aug. 28, 2001) describe chemical, structural, and physiological variations that produce dramatic and nonlinear changes in the optical properties of the tissue sample. The measurement is further complicated by the heterogeneity of the sample, the multi-layered structure of the skin, rapid variation related to hydration levels, changes in the volume fraction of blood in the tissue, hormonal stimulation, temperature fluctuations, and variation of blood constituent concentrations. These issues are further considered through a discussion of the scattering properties of skin.

Tissue Scattering Properties

Skin Structure

The structure and composition of skin varies widely among individuals. In addition, skin properties vary at different sites and over time on the same individual at the same site. The outer layer of skin comprises a thin layer known as the stratum corneum, a stratified cellular epidermis, and an underlying dermis of connective tissue. Below the dermis is the subcutaneous fatty layer or adipose tissue. The epidermis is the thin outer layer that provides a barrier to infection and loss of moisture, while the dermis is the thick inner layer that provides mechanical strength and elasticity. The epidermis layer is 10 to 150 µm thick and is divided into three layers, the basal, middle, and superficial layers. The basal layer borders the dermis and contains pigment-forming melanocyte cells, keratinocyte cells, langherhan cells, and merkel cells. In humans, the thickness of the dermis ranges from 0.5 mm over the eyelid to 4 mm on the back and averages approximately 1.2 mm over most of the body.

In the dermis, water accounts for approximately seventy percent of the volume. The next most abundant constituent is collagen, a fibrous protein comprising 70 to 75 percent of the dry weight of the dermis. Elastin fibers, also a protein, are plentiful though they constitute only a small proportion of the bulk. In addition, the dermis contains a wide variety of structures, such as sweat glands, hair follicles, blood vessels, and other cellular constituents. Conversely, the subcutaneous layer, adipose tissue, is by volume approximately ten percent water and includes primarily cells rich in triglycerides and/or fat. The concentration of glucose varies in each layer according to the water content, the relative sizes of the fluid compartments, the distribution of capillaries, and the perfusion of blood. Due to the high concentration of fat and fats tendency to repel water and glucose that water carries, the average concentration of glucose in subcutaneous tissue is significantly lower compared to the glucose concentration in the dermis.

Optical Properties of Skin

When near-infrared light is delivered to the skin, a percentage of it is reflected while the remainder penetrates into the skin. The proportion of reflected light, specular reflectance, is typically between four to seven percent of the delivered light over the entire spectrum from 250 to 3000 nm, for a perpendicular angle of incidence. The 93 to 96 percent of the incident light that enters the skin is attenuated due to absorption or scattering within the many layers of the skin. These two processes taken together essentially determine the penetration of light into skin, the tissue volume that is sampled by the light, and the transmitted or remitted light that is scattered from the skin.

Diffuse reflectance or remittance is defined as that fraction of incident optical radiation that is returned from a turbid sample. Alternately, diffuse transmittance is the fraction of incident optical radiation which is transmitted through a turbid sample. Absorption by various skin constituents account for the spectral extinction of the light within each layer. Scattering is the process by which photons are redirected to the skin surface to contribute to the observed diffuse reflectance of the skin.

Scattering in tissue is due to discontinuities in the refractive index on the microscopic level, such as the aqueous-lipid membrane interfaces between each tissue compartment or the collagen fibrils within the extracellular matrix.

The spatial distribution and intensity of scattered light depends upon the size and shape of the particles relative to the wavelength and upon the difference in refractive index between the medium and the constituent particles. The scattering of the dermis is dominated by the scattering from collagen fiber bundles in the 2.8 µm diameter range occupying 21 percent of the dermal volume and the refractive index mismatch is 1.38/1.35. The spectral characteristics of diffuse remittance from tissue are the result of a complex interplay of the intrinsic absorption and scattering properties of the tissue, the distribution of the heterogeneous scattering components, and the geometry of the points of irradiation relative to the points of light detection.

Absorbance of light in tissue is primarily due to three fundamental constituents: water, protein, and fat. As the main constituent, water dominates the near-infrared absorbance above 1100 nm and is observed through pronounced absorbance bands. Protein in its various forms, and in particular collagen, is a strong absorber of light that irradiates the dermis. Near-infrared light that penetrates to subcutaneous tissue is absorbed primarily by fat. In the absence of scattering, the absorbance of near-infrared light due to a particular analyte, A, is approximated by Beers Law at each wavelength according to:

$$A=\epsilon bC \quad (1)$$

where $\epsilon$ is the analyte specific absorption coefficient, C is the concentration, and b is the pathlength. The overall absorbance at a particular wavelength is the sum of the individual absorbances of each particular analyte given by Beer's Law. The concentration of a particular analyte, such as glucose, can be determined through multivariate analysis of the absorbance over a multiplicity of wavelengths because $\epsilon$ is unique for each analyte. However, in tissue compartments expected to contain glucose, the concentration of glucose is at least three orders of magnitude lower than that of water. Consequently, the signal targeted for detection by reported approaches to near-infrared measurement of glucose concentration, the absorbance due to glucose in the tissue, is expected to be at most three orders of magnitude less than other interfering tissue constituents. Therefore, the near-infrared measurement of glucose concentration requires a high level of sensitivity over a broad wavelength range and the application of methods of multivariate analysis.

The diverse scattering characteristics of the skin cause light returning from an irradiated sample to vary in a highly non-linear manner with respect to tissue analytes and in particular glucose. Simple linear models, such as Beer's Law, are invalid for analysis of highly scattering matrices, such as the dermis. This is a recognized problem and several reports have disclosed unique methods for compensating for the nonlinearity of the measurement while providing the necessary sensitivity [E. Thomas, R. Rowe, Methods and Apparatus for Tailoring Spectroscopic Calibration Models, U.S. Pat. No. 6,157,041 (Dec. 5, 2000)].

Dynamic Properties of Skin

While knowledge and use of the optical properties of the skin, high instrument sensitivity, and compensation for the inherent nonlinearities are vital for the application of near-infrared spectroscopy to noninvasive blood analyte measurement, an understanding of biological and chemical mechanisms that lead to time dependent changes in the optical properties of skin tissue is equally important and yet largely ignored. At a given measurement site, skin tissue is often assumed to be static except for changes in the target analyte and other absorbing species. However, variations in the physiological state of tissue profoundly effect the optical properties of tissue layers and compartments over a relatively short period of time. Such variations, are often dominated by fluid compartment equalization through water shifts and are related to hydration levels and changes in blood analyte levels.

Total body water accounts for over sixty percent of the weight of the average person and is distributed among two major compartments: the extracellular fluid, which comprises one-third of total body water, and the intracellular fluid, which comprises two-thirds of total body water. The extracellular fluid, in turn, is divided into the interstitial fluid (extravascular) and the blood plasma (intravascular). Water permeable lipid membranes separate the compartments and water is transferred rapidly between them through diffusion to equalize the concentrations of water and other analytes across the membrane. Water flux from one compartment to another is driven by osmosis and the amount of pressure required to prevent osmosis is called the osmotic pressure. Under static physiological conditions the fluid compartments are at equilibrium. However, during a net fluid gain or loss as a result of water intake or loss, all compartments gain or lose water proportionally.

Distribution of substances contained in blood serum that are needed by the tissues, such as water and glucose, occurs through the process of diffusion. The movement of water and other analytes from intravascular to extravascular compartments occurs rapidly as tremendous numbers of water and other molecules, in constant thermal motion, diffuse back and forth through the capillary wall. On average, the rate at which water molecules diffuse through the capillary membrane is about 80 times greater than the rate at which the plasma itself flows linearly along the capillary. The actual diffusion rate is proportional to the concentration difference between the two compartments and the permeability of the molecule. Water, for example, is approximately 1.7 times more permeable than glucose.

Short-term changes in blood glucose concentration lead to a corresponding change in blood osmolality. Fluid is rapidly re-distributed accordingly and results in a change in the water concentration of each body compartment. For example, the osmotic effect of hyperglycemia is a movement of extravascular, i.e. cell and interstitial fluid, water to the intravascular space. Conversely, a decrease in blood glucose concentration leads to a movement of water to extravascular space from the intravascular compartment.

Because the cell membrane is relatively impermeable to most solutes but highly permeable to water, whenever there is a higher concentration of a solute on one side of the cell membrane, water diffuses across the membrane toward the region of higher solute concentration. Large osmotic pressures can develop across the cell membrane with relatively small changes in the concentration of solutes in the extracellular fluid. As a result, relatively small changes in concentration of impermeable solutes in the extracellular fluid, such as glucose, can cause tremendous changes in cell volume. These changes in cell volume are observed in noninvasive near-infrared spectra of tissue.

Several methods are reported to compensate in some part for the dynamic variation of the tissue. For example, K. Hazen, *Glucose determination in biological matrices using near-infrared spectroscopy*, Doctoral Dissertation, University of Iowa, (August 1995) and J. Burmeister *In-vitro model for human noninvasive blood glucose measurements*, Doctoral Dissertation, University of Iowa (December 1997) describe several methods of noninvasive glucose measurement that use calibration models that are specific to an individual over a short period of time. This approach avoids modeling the differences between patients and therefore does not generalize to more individuals. However, the calibration models have not been tested over long time periods, do not provide means for compensating for the varying optical properties of the sample, and do not address variation related to the dynamic water shifts of fluid compartments.

Malin, supra, reports a method for compensating for variation related to the structure and state of the tissue through an intelligent pattern recognition system capable of determining calibration models that are most appropriate for the patient at the time of measurement. The calibration models are developed from the spectral absorbance of a representative population of patients that have been segregated into groups. The groups or classes are defined on the basis of structural and state similarity such that the variation within a class is small compared to the variation between classes. Classification occurs through extracted features of the tissue absorbance spectrum related to the current patient state and structure. However, the invention does not use features for directly compensating for physiological changes in the tissue. Further, the direct use of features representing the physiological state of the subject's measurement site for noninvasive measurement of glucose was not described.

Thomas, supra, identifies a method for reducing intra-subject variation through the process of mean-centering both the direct and indirect measurements. However, this does not address the key problem related to sample heterogeneity and complexity, physiological and chemical variation related to the dynamic nature of the tissue, and the common problem of optical variation which occurs from sample-to-sample.

Several approaches exist that employ diverse preprocessing methods to remove spectral variation related to the sample and instrument variation including multiplicative signal correction (P. Geladi, D. McDougall, H. Martens *Linearization and scatter-correction for near-infrared reflectance spectra of meat*, Appl. Spect., vol. 39, pp. 491-500 (1985)), standard normal variate transformation (R. J. Barnes, M. Dhanoa, S. Lister, Appl. Spect., vol. 43, pp. 772-777 (1989)), piecewise multiplicative scatter correction (T. Isaksson, B. Kowalski, Appl. Spect., 47, pp. 702-709 (1993)), extended multiplicative signal correction (H. Martens, E. Stark, J. Pharm Biomed Anal, vol. 9, pp. 625-635, (1991)), pathlength correction with chemical modeling and optimized scaling (T. Isaksson, Z. Wang, B. Kowalski, J. Near Infrared Spect., vol. 1, pp. 85-97 (1993)), and finite impulse response (FIR) filtering, (S. Sum, *Spectral signal correction for multivariate calibration*, Doctoral Dissertation, University of Delaware, (Summer 1998); S. Sum, S. Brown, *Standardization of fiber-optic probes for near-infrared multivariate calibrations*, Appl. Spect., vol. 52, no. 6, pp.869-877 (1998); and T. Blank, S. Sum, S. Brown, S. Monfre *Transfer of near-infrared multivariate calibrations without standards*, Analytical Chemistry, vol. 68, pp. 2987-2995 (1996)).

Sum (summer 1998), supra, further describes a practical solution to variation due to changes in a given physical sample and instrument effects through the use of signal preprocessing techniques. The reported methods reduce the variance in the spectral measurement arising from non-chemical sources while retaining the variance caused by chemical change. The sources of variance include the physical traits of the sample, such as, particle size and shape, packing density, heterogeneity, and surface roughness. The methods include preprocessing through a derivative step followed by a spectral transformation through either multiplicative scatter correction or standard normal variate transformation.

In addition, a diversity of signal, data or pre-processing techniques are commonly reported with the fundamental goal of enhancing accessibility of the net analyte signal. The net analyte signal refers to the portion of the spectral signal related to the target analyte that is orthogonal to the interference (A. Lorber, K. Faber and B. Kowalski, *Net analyte signal calculation in multivariate calibration*, Anal. Chem, vol. 69, pp. 1620-1626, (1997); A. Oppenheim, R. Schafer, *Digital signal processing*, Englewood Cliffs, N.J.: Prentice Hall, pp. 195-271 (1975); and A. Savitzky, M. Golay *Smoothing and differentiation of data by simplified least squares procedures*, Anal. Chem., vol. 36, no. 8, pp.1627-1639 (1964)).

Problem Statement

While known methods for preprocessing effectively compensate for variation related to instrument and physical changes in the sample and enhance the net analyte signal in the presence of noise and interference, they are as reported inadequate for compensating for the sources of tissue related variation defined above. For example, highly nonlinear effects related to sampling different tissue locations cannot be effectively compensated for through a pathlength correction because the sample is multi-layered and heterogeneous. In addition, fundamental assumptions inherent in these methods, such as the constancy of multiplicative and additive effects across the spectral range and homoscadasticity of noise are violated in the noninvasive tissue application. In particular, re-distribution of water between various tissue compartments alter the optical properties of the tissue through changes in the water concentration, the concentration of other analytes, the refractive indices of various layers, the thickness of tissue layers, and the size and distribution of scattering centers. Therefore, the optical properties of the tissue sample are modified in a highly nonlinear and profound manner. In addition, the actual tissue volume sampled and the effective or average pathlength of light is varied. No method for preprocessing a near-infrared spectral measurement is reported that effectively compensates for the complex, heterogeneous, layered, and dynamic composition of tissue; the profound variation over time, from sample-to-sample and between patients; and the changes in optical properties related to the re-distribution of water between various tissue compartments.

SUMMARY OF THE INVENTION

This invention provides a method and apparatus that corrects for tissue related interference calibration and/or measurement of biological parameters noninvasively. The invention concerns such terms as outlier identification, filtering, spectral correction, and baseline subtraction steps that, when used together, provides for noninvasive measurement of biological parameters, such as glucose concentration.

DETAILED DESCRIPTION OF THE INVENTION

The invention comprises a method and apparatus for processing near-infrared tissue measurements. More particularly, the invention detects outliers, optimally or near-optimally filters, provides spectral correction, and performs background removal to enable the noninvasive measurement of biological parameters, such as glucose concentration. The method and apparatus are further described, infra.

Results obtained through the use of a processing system are highly dependent upon the order of the individual operations. This is a consequence of the nonlinear nature of the correction step and the influence that the outlier detection step has on the final results. As a result, superposition of the operations does not apply and any re-ordering causes a different outcome.

Apparatus

The invention comprises a noninvasive analyzer, which includes a spectroscopic measurement system, a sample interface module, and a computational analyzer. The spectroscopic measurement system detects the diffusely transmitted or reflected near-infrared radiation, within a specified range, from the targeted tissue; and the analyzer corrects the measured spectrum for calibration and/or measurement of target biological parameters, properties, constituents, or analytes. The spectroscopic measurement system includes a source of near-infrared radiation, a wavelength selection system, an interface to the sample, including a radiation delivery and recovery system, a means for analyzing the detected near-infrared radiation and, preferably, a means for displaying the measured analyte, property, or constituent. The source radiates near-infrared energy, such as the wavelength range about 700 to 2500 nm and is, for example, an array of light emitting diodes (LEDs) or a broadband lamp, such as a halogen lamp. In the case of a broadband source, an optical filter is optionally used to reduce the effects of energy at wavelengths not in the spectral range of interest, but that are emitted by the source of near-infrared energy. A method of wavelength separation before and/or after illumination of the sample is used with a broadband source. Examples include a set of filters, a dispersive element, such as a plane, concave, ruled, or holographic grating, and an interferometer. Alternative techniques include successive illumination of the elements of an LED array or a Hadamard transform spectrometer. The sensing element is one or more detectors, which are responsive to the targeted wavelengths.

Figure 1:
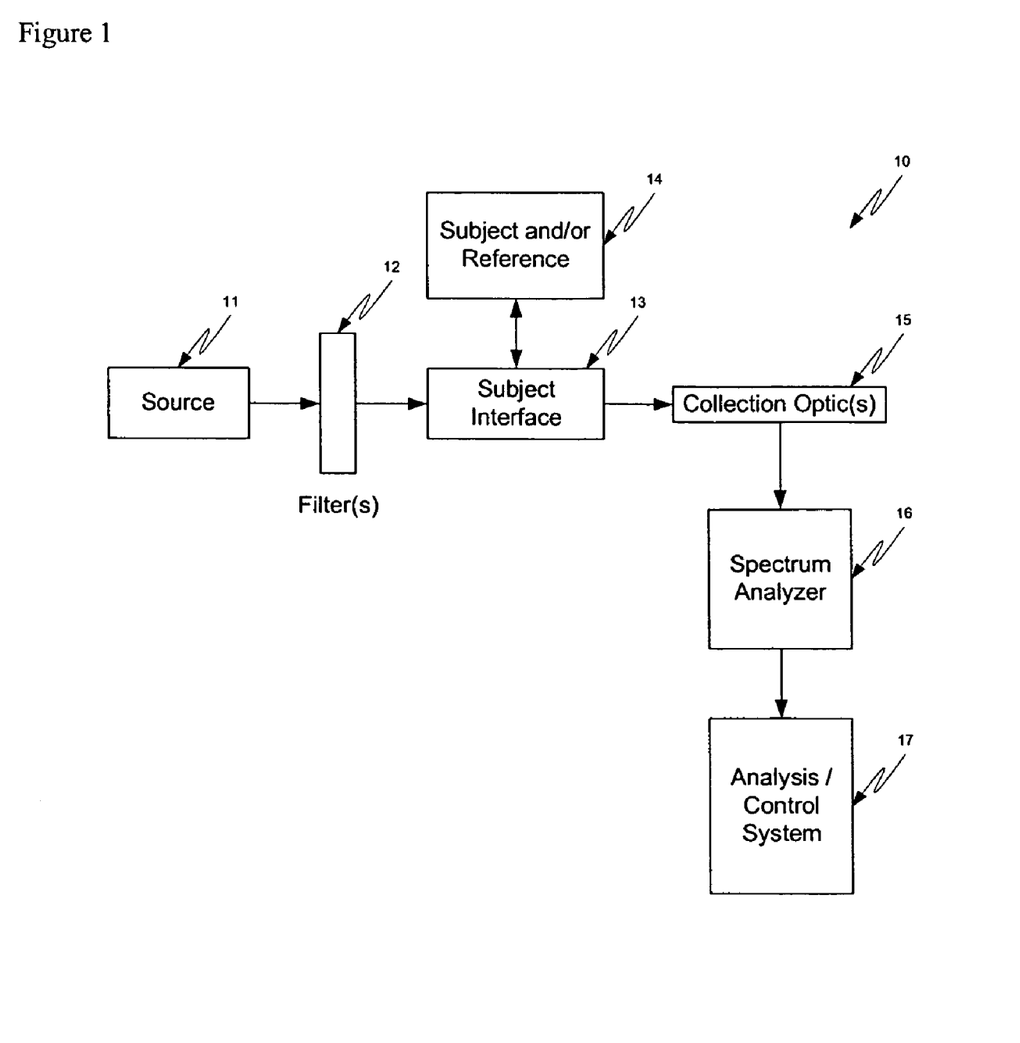
FIG. 1 provides a block diagram of a noninvasive analyzer according to the invention.

Referring now to FIG. 1, an exemplary embodiment of an analyzer 10 is illustrated in block diagram form. This example includes a source 11, such as a tungsten halogen lamp or array of LEDs, an optical filter 12 for removing light at unnecessary wavelengths and/or to avoid heating, a subject interface system 13, a means for collecting light 15 and coupling it to the spectrum analyzer, such as one or more detection fibers, a spectrum analyzer 16 or spectrometer for determining the intensity of light at each wavelength e.g. a grating and an array of detectors, and a control and analysis system 17, described infra. Optional items of the analyzer 10 include means for collecting dark current and spectra of x- and/or y-axes standards. For example, an actuated light blocker for measurement of the detector dark current is used and an actuated standardization material, such as polystyrene is used. Additional spectrometer configurations and embodiments are described in U.S. patent application Ser. No. 10/472,856, filed Mar. 7, 2003, which is incorporated herein in its entirety by this reference thereto.

The interface to the sample 13 comprises an interface module that directs near-infrared radiation to and from the sample either directly or through a light pipe, fiber-optics, one or more filters, a lens system, or a light directing mirror system. The area of the tissue surface to which near-infrared radiation is applied, and the area of the sample surface from which returning near-infrared radiation is detected, are preferably different and separated by a defined distance selected to target a tissue volume conducive for the measurement of the property of interest. The collected near-infrared radiation is converted to a voltage and sampled through an analog-to-digital converter for analysis on a microprocessor based system and the result computed.

Processing

Figure 2:
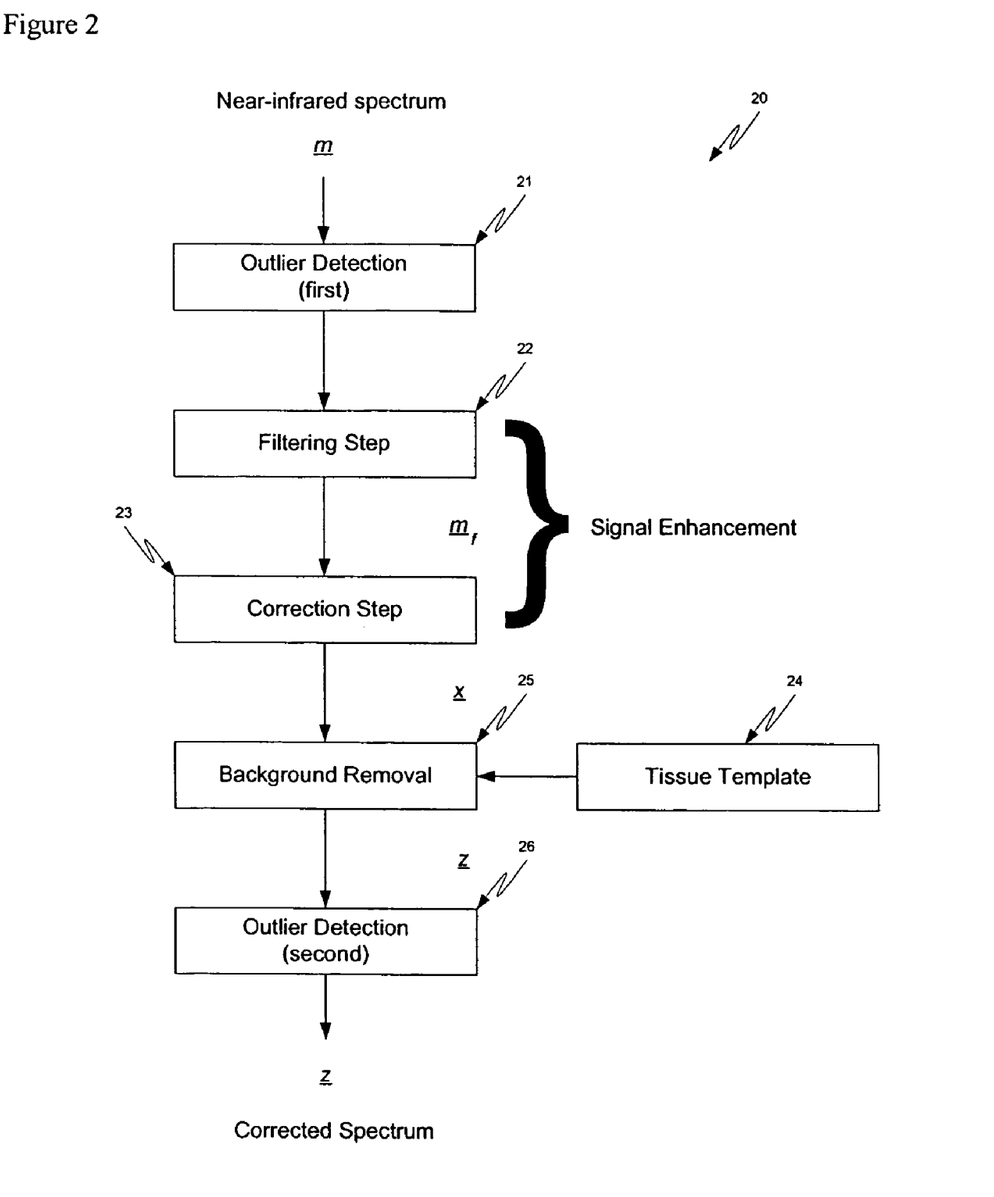
FIG. 2 provides a block diagram of an analysis method according to the invention.

Referring now to FIG. 2, a block diagram summarizing processing 20 of the near-infrared signal is presented. The order of operations presented in FIG. 2 is optimal for the application of noninvasive analysis of a tissue property, such as noninvasive glucose concentration estimation. Changing the order of the processing changes the results. The method optionally includes both gross 21 and detailed 26 methods for detecting outliers or anomalous measurements that are incompatible with the processing methods or are the result of sampling or instrument errors. Spectral correction, involving the steps of filtering 22 and/or correction 23, is applied to compensate for noise and interference and to adjust a spectrum according to local or minor changes in the optical properties of the tissue sample. The step of background removal 25 reduces variation in the measurement, such as variation associated with sample-site differences, dynamic tissue changes, and subject-to-subject variation. The tissue template 24 is used to remove background 25. Examples of a tissue template include a spectrum of the subject, a basis set, or a spectrum computed from a cluster. Exemplar processing steps are described, infra.

Spectral Measurement

The spectrometer system provides a spectral measurement or spectrum to the analyzer for determination or measurement of the concentration of glucose. The spectrum is denoted by the vector $m \in \Re^{1 \times N}$ of absorbance values pertaining to a set of N wavelengths $\lambda \in \Re^N$ that span the near-infrared, such as about 700 to 2500 nm or ranges therein. In the preferred embodiment, the measurement process and absorbance calculation is as follows: the light intensity measured from the tissue, $I \in \Re^{1 \times N}$, and the light intensity measured from a non-absorbing reference material, $I_o \in \Re^{1 \times N}$, are used to determine m according to:

$$m = -\log_{10}\left(\frac{I}{I_o}\right) \quad (2)$$

where m is the reflectance spectrum of the skin and is analogous to an absorbance spectrum containing quantitative information that is based on the known interaction of the incident light with components of the body tissue. More particularly, however, the measurement includes a set of wavelengths in the near infrared that have been optimized for the extraction of features and the measurement requirements. For example, the measurement of glucose is optionally performed in the wavelength range about 1100 to 1935 nm or a selected subset of wavelengths.

Alternately, the spectral measurement is determined according to $$m = -\log_{10}\left(\frac{I}{I_r}\right) \quad (3)$$

where $I_r \in \Re^{1 \times N}$ is a representation of the measured tissue intensity at some point in time prior to collection of I and can be determined from a single tissue intensity spectrum or from the mean or a robust estimate of the mean, such as a trimmed mean, of several tissue intensity spectra. In another embodiment, the measurement m, can be defined as the measured intensity, I. Alternatively, m is a single spectrum collected from an instrument, a cluster, or a combination of several optimally selected spectra collected over a defined measurement period and averaged. The methods for selecting the spectra are used to produce the lowest noise measurement and include similarity measures, distance measures, and clustering operations.

Gross Outlier Detection

The initial outlier detection step removes aberrant spectra that 1) would not be easily detected if performed after filtering, and 2) would be highly detrimental to the correction step magnitude calculation. Gross error detection executed in the steps immediately following the measurement of a spectrum is performed on the basis of specifications common to all samples and involves rudimentary tests for data acceptability. The tests for acceptability are made on the basis of specifications for noninvasive glucose measurement. If a deviation from the specified level of acceptability is detected the resulting action is the rejection of the collected spectrum, the rejection of the entire sample, or the generation of an instrument malfunction error.

The errors detected include both instrument and sampling errors. Instrument errors are detected on the basis of performance specifications, such as noise, signal level, wavelength accuracy and precision, stray light, linearity and measurement stability. Examples of sampling errors include imprecision, tissue transients, tissue distortion, and poor surface contact. For example, poor surface contact is detected when the measured absorbance exceeds a preset limit in the wavelength regions surrounding 1450 and 1950 nm.

Signal Enhancement

One step of the invention used for noninvasive measurement of biological parameters, agents, chemicals, properties, and constituents or analytes is a method that attenuates or removes the signal related to spectrally manifested changes or interference in the sampled tissue while substantially passing the net analyte signal of the target analyte.

The method is preferably performed on spectroscopic data collected by the apparatus before generating a calibration model and before measuring using the sensor. Calibration is performed through a calibration data set of exemplary paired data points from one or more subjects collected over a period of time. Each paired data point comprises a spectroscopic measurement, or spectrum, and a corresponding reference value for the analyte of interest. The calibration is any of a mathematical model, equation, or a curve that is developed on the basis of the calibration set, and is used subsequently to determine the value of the analyte on the basis of a spectroscopic measurement. The invented method of spectral correction has been found to be beneficial for correction of both the spectroscopic data used for calibration and for subsequent measurement.

Without loss of generality, the primary effects that are addressed by the disclosed spectral correction steps are changes in the optical properties of the tissue resulting from fluid or water shifts occurring between the various compartments in tissue. However, the method reduces variation related to many other types of tissue related variation, including surface reflectance, changes in sample probe position, tissue hydration, tissue temperature, changes in probe pressure, and changes in the rates of tissue blood perfusion. These tissue changes are manifested spectrally, in part, through baseline variation and a nonlinear multiplicative distortion of the spectrum related to changes in the pathlength of the near-infrared radiation and an inner filter effect. Three main signal enhancement steps, use of net analyte signal, filtering, and/or correction, are identified that greatly reduce and compensate for the nonlinear distortion and are described, infra.

Net Analyte Signal

Net analyte signal is determined apriori and represents the unique variation in the spectral signal related to the target analyte property in the presence of interference. Preprocessing steps are optimized to maximize the ratio of net analyte signal to noise. Generally, this is done empirically, through modeling, simulation, or theoretically by imposing the characteristics of or applying directly the preprocessing steps upon the known net analyte signal and related noise. For example, the break frequency of a low-pass filter is optimized to pass the signal of the analyte while attenuating the high frequency noise components. In a second example, a high-filter or bandpass cut-off parameters pass signal while restricting low frequency noise or both high and low frequency noise components, respectively. In yet another example, the wavelength range of multivariate scatter correction is selected based upon the ratio of signal to noise on a wavelength by wavelength basis. In still yet another example, in cases where the noise involves significant interference a background subtraction step using the net analyte signal is optimized to remove noise relative to signal Filtering The first signal enhancement method, step, or operation, denoted filtering, removes the low frequency or baseline variation, such as changes resulting from variation in the reduced scattering coefficient and/or surface reflectance. The step is accomplished through the application of a band-pass filter across the wavelength axis of the measured spectrum, which performs two basic functions. First, the low frequency variation over the wavelength axis of the measured spectrum is attenuated through a high-pass filtering operation. The cut-off frequency or bandwidth of the high-pass operation is determined according to the level of low-frequency interference and the frequency content of the net analyte signal of the targeted analyte. The second function is a low-pass or smoothing operation in which noise is suppressed through the attenuation of higher frequencies. The break frequency of the low-pass filter is set according to the bandwidth of the spectrometer, the net analyte signal of the target analyte or constituent, and the necessary signal-to-noise ratio required to make the measurement. The two functions can be performed simultaneously or one at a time, in either order, depending on the implementation of the band-pass filter. The methods used for performing this operation comprises infinite-impulse response (IIR) and finite-impulse response (FIR) band-pass filtering. In the preferred embodiment, a FIR filter is implemented according to $$m_{f,j} = \sum_{k=1}^{P} a_k m_{j-k-\frac{(p-1)}{2}} \tag{4}$$

where $m_{f,j}$ is the filtered spectrum at the jth measured wavelength, $m_j$ is the measured spectrum at the jth wavelength, $a_k$ denotes the kth filter coefficient and P is the length of the filter impulse response or filter window width. In the equation, the filter is non-causal and applied across the wavelength axis of the measured spectrum. The filter width P is assumed to be an odd number and the filter coefficients are determined according to the desired filter break frequencies and characteristics of the pass and stop-bands. In a preferred embodiment, a Savitsky-Golay first derivative determines the filter coefficients with a smoothing window selected based on the noise characteristics, spectral sampling interval, and instrument bandwidth. In one application of the process for the measurement of glucose, a 31 nm smoothing window was determined to be optimal, although window sizes between 15 and 61 nm were also determined to be effective. Alternately, the FIR filter design and coefficient determination is performed through one of many existing techniques, such as truncation and tapering of a target infinite impulse response sequence.

In an alternate embodiment of the filtering operation, when the sampling interval is large, such as when the wavelength discretization of the spectrum is course and/or the signal-to-noise ratio is sufficient, only the high-pass filtering operation is performed. A special case of the FIR high-pass filter is used in the form of a first difference of the spectrum.

In a preferred embodiment of the invention, the measured spectrum is oversampled with respect to the wavelength axis and the low-pass bandwidth is set equal to the optical bandwidth of the spectrometer. However, the break frequency of the low-pass section is optionally determined through an analysis of the signal-to-noise ratio, where the net analyte signal is the signal and the noise is the root-mean-square variation of the measured spectrum in the wavelength region used for measurement of the target analyte. As the low-pass bandwidth is reduced, the high frequency components of the noise are attenuated leading to a reduction in the noise. However, this process also attenuates high frequency components of the signal leading to a simultaneous reduction in the net analyte signal. In cases in which the spectrum is oversampled with respect to the wavelength axis, the noise is distributed in greater proportions at higher frequencies than the net analyte signal. Therefore, low-pass filtering the measured spectrum removes a greater proportion of the noise than the net analyte signal. The optimal low-pass bandwidth is defined as one that maximizes or increases the ratio of the net analyte signal to the noise. Given a frequency domain model including the net analyte signal, NAS(f), and the noise, N(f), the bandwidth of the low-pass filter, $f_{bw}$, is determined through $$SNR(f_{bw})^2 = \frac{\sum_{f=0}^{f_{bw}} |NAS(f)|^2}{\sum_{f=0}^{f_{bw}} |N(f)|^2} \quad (5)$$

as the value for $f_{bw}$ at which $SNR(f_{bw})$ is maximized. Alternately, this process is performed iteratively by filtering a wavelength domain representation of the net analyte signal and noise at various low-pass bandwidths or through an empirical set of data by selecting the break frequency to optimize the standard error of prediction or other figure of merit.

The break frequency of the high-pass section is set to attenuate low frequency variations caused by changes in the scattering, while passing the net analyte signal. This is generally accomplished empirically through an exemplary set of data or through a harmonic analysis of the net analyte signal.

Correction

A second signal enhancement step is a correction step that generally involves a magnitude adjustment which is derived from the shape of the target spectrum. Correction is preferably performed after filtering. If correction is performed prior to filtering, the magnitude calculation becomes heavily influenced and degraded by signal components that obscure the analytical signal of interest. Therefore, the optimal point to correct each spectrum is after the removal via filtering of the signal components that are destructive and/or negatively influence the analytical signal.

In the general case, the correction occurs through the transformation $$x = g(m_f, m_r) \quad (6)$$

where $m_f$ is the filtered spectral measurement, $m_r$ is a reference filtered spectral measurement derived from a calibration data set or is estimated from one or more previously collected and filtered spectral measurements and the function $g(\bullet)$ is a linear or nonlinear transformation. In the common linear case, the principle of correction is to normalize the filtered spectrum through a scaling factor and, optionally, an offset correction according to $$x = a + m_f b^T \quad (7)$$

where $m_f$ is the filtered spectral measurement, x is the corrected measurement and a and b are the offset and scaling adjustments respectively. The scaling factor a and/or the offset b are scalars or are determined and different at each individual wavelength. In the latter case both a and b are 1-by-N vectors. Methods for performing these operations include multiplicative scatter correction, extended multiplicative signal correction, piecewise multiplicative scatter correction, standard normal variate transformation, pathlength correction with chemical modeling and optimized scaling, FIR filtering, division by the norm, such as the Euclidean distance of the filtered measurement, division by the filtered spectral measurement at a single wavelength, or division by the filtered spectral measurement determined from the difference of two wavelengths.

In the preferred embodiment, multiplicative scatter or pathlength correction is applied through a rotation that fits the filtered spectral measurement, $m_f$, to a reference spectrum, $m_r$, that is derived from a calibration data set or is estimated from an earlier group of filtered spectral measurements. First, the spectrum is fit via linear regression or weighted linear regression based upon noise according to $$m_{f,j} = a + b m_{r,j} \quad (8)$$

where a and b are the offset and scaling adjustments respectively, such as slope and intercept, and j is a set of M selected wavelengths. The spectrum is then corrected through $$x = (m_f - a)/b \quad (9)$$

where x is the final filtered and corrected spectral measurement.

An important part of the determination of a and b is the selection of the M wavelengths. The wavelengths used are determined to maximize the accessibility of the net analyte signal of the target analyte in x. While all wavelengths, or elements, of $m_f$ are optionally used, the preferred approach is to select the region or regions where the net analyte signal of the target analyte is the greatest and where ancillary effects, such as surface reflectance, cause the least amount of spectral distortion. For example, in the case of the noninvasive measurement of glucose the wavelength range selected for use is about 1100 to 1850 nm and/or about 2050 to 2350 nm. Alternate regions include regions about 1100 to 1350 nm, about 1650 to 1800 nm, and about 2100 to 2300 nm. Modest variations, such as up to 100 nm, to these specific wavelength are possible without a significant change in the results. In addition, the wavelength ranges are optionally expanded or contracted based upon the stability of the tissue that is spectroscopically sampled and/or the dynamic range of the instrument.

In an alternative embodiment, a modified standard normal variate transformation is used to normalize the spectrum according to the equation $$x = (m_f - a)/b \tag{10}$$

where x is the final filtered and corrected spectral measurement, $m_f$ is the filtered spectral measurement, and a is an offset, such as the mean of $m_f$ over specific wavelengths, and b is the standard deviation of $m_f$ over specific wavelengths. The variables a and b are calculated according to $$a = \frac{1}{M}\sum_{i=1}^{M} m_{f,j(i)} \qquad b = \sqrt{\frac{1}{M-1}\sum_{i=1}^{M}(m_{f,j(i)} - a)^2} \tag{11}$$

where M is the number of selected wavelengths and j is a n 1-by-M vector corresponding to the selected wavelengths. In the equation, $m_{f,j(i)}$ refers to the filtered spectral measurement at wavelength j(i). The set of wavelengths, j, is an important part of the correction steps of this alternative embodiment. The preferred method is to select the wavelength range targeted for the measurement of the target analyte and avoid regions not conducive to the measurement of the analyte. These include wavelength ranges where nonlinearities associated with the dynamic range of the instrument are present, such as about 1400 to 1550 nm, about 1880 to 2050 nm, and wavelength ranges in which the dynamic nature of the tissue profound effects the spectral measurement.

The two main signal enhancement steps provide a corrected spectrum x with respect to volumetric and pathlength distortions related to fluid compartment transients and other effects that influence that optical properties of tissue. The order of the steps is preferably filtering and then correcting because this order optimizes subsequent measurements or estimations. Use of the steps in reverse order or singly is possible, with degraded results.

Background Removal

As noted previously, existing methods, such as multiplicative scatter correction and standard normal variate transformation, are used with the assumption that the multiplicative and additive sources of variation are uniform across the entire spectrum. However, in many applications, such as noninvasive measurement of glucose concentration, variation in the spectra in not corrected in this manner. Therefore, a step for correcting the non-linear variation resulting from sampling site differences that results from the heterogeneity and layered composition of the sample is provided.

The background removal step uses a basis set of spectral interferences to remove the signals that are specific to a given sampled tissue volume, i.e. the background. The optical estimate of the background is preferably performed subsequent to the removal of noise and the correction of the spectrum. If this operation is implemented prior to spectral correction, detrimental signal components detrimental remain in the spectrum that compromise the estimate of the background and lead to degraded results.

A background removal step preferably follows the steps defined above and uses a spectral background or tissue template. For example, the background removal step performed by calculating the difference between the estimated spectral background or tissue template and x through $$z = x - (cx_t + d) \tag{12}$$

where $x_t$ is the estimated background or tissue template, c and d are slope and intercept adjustments to the tissue template. Direct subtraction is just one form of background removal. The spectrally corrected signal z is used for calibration development or measurement of a target analyte. The background is estimated on the basis of an optimal selection of spectrally corrected measurements collected prior to the measurement m. The variables c and d are preferably determined on the basis of features related to the dynamic variation of the tissue. In one embodiment, $x_t$ is a spectrally corrected spectral measurement collected on tissue at the beginning of a measurement period. The measurement period is defined as a time period during which the state of the tissue sample is uniform.

When a large data set exists for processing, the background is optionally determined as the mean of data cluster defined according to similarity. In the case of noninvasive glucose measurement, the data clusters represent spectra collected from the same patient over a relatively short period of time, such as one-day, on one tissue sample site.

Break frequencies of the filtering system or the wavelength regions vary both from application to application, depending upon the net analyte signal, and from subject to subject. Malin, supra, disclosed various classes of skin tissue are optionally determined, each with an optimized calibration. Similarly, the spectral correction system is customized to each patient, patient sub-group, time period, or application.

While the embodiment of the spectral correction system is for the special case of a spectral measurement with a 1-by-N dimension, the steps are readily applicable to spectral measurements that have P-by-N dimension where the dimensions P and N correspond to variables, such as wavelength, time, or position. Specifically, the spectroscopic measurements of a near-infrared imaging system are optionally corrected according to the process disclosed.

Finally, the disclosed invention is applicable to a variety of applications in addition to skin tissue and is optionally used to correct for the nonlinear distortion of turbid materials for the near-infrared measurement of analytes. For example, the spectral correction system is directly applicable to the analysis of blood for the determination of blood analyte properties. Similarly, the determination of the constituents of solid or liquid samples can be improved through the disclosed invention.

Enhanced Outlier Detection

Prior to the generation or application of a calibration model, enhanced outlier detection is performed to detect and remove spectra that are inconsistent with the expected structure and variance of the data. Therefore, a comparison between the processed measurement and a known and accepted set of specifications is performed through distance measures and/or a cluster analysis. In the preferred embodiment, the detection of spectral outliers is performed through a principal components analysis and an analysis of the residuals. First, the processed measurement z is projected onto a set of eigenvectors, contained in the matrix O, that were developed through a principal components analysis on the calibration set. The number of eigenvectors varies from 2 to 75 and is dependent on the specific calibration set. The projection of the processed spectrum z onto the eigenvectors proceeds according to $$xpc_o = zO \tag{13}$$

and produces a 1 by P vector of scores, $xpc_o$. The residual, $f_{h,1}$, is determined according to $$f_{h,1} = \|x - xpc_o O^T\|. \tag{14}$$

An error condition occurs if the result is greater than a specification cut-off, such as three times the standard deviation of the expected residual.

Alternately, the root-mean-square of the scores is calculated, either on the raw scores or after variance scaling the scores, to generate a distance metric. The distance metric is compared to a preset limit and/or to the distance of recent samples to detect an erroneous measurement.

Finally, the distance metric of a particular sample is optimally compared to preceding samples. If a large change, such as an increase, in the distance metric from one or more prior samples to the current sample is observed an outlier is detected.

EXAMPLE I

In one example, the following steps are performed to process the spectra:
- averaging spectra;
- correcting dead pixels;
- calculating absorbance;
- performing x-axis standardization;
- uniformly re-sampling the spectrum to standardize the x-axis;
- performing a first (gross) outlier detection;
- correcting the spectrum;
- performing a wavelength selection;
- removing interference; and
- performing a second (fine) outlier detection.

The order of the steps is optionally varied to a limited degree. For example, the wavelength selection step is optionally performed out of sequence, such as after the second outlier detection or before any of the earlier steps. In addition, not all steps are required. For example, correcting dead pixels is not appropriate to some analyzers. As a second example, conversion to absorbance is not always required, nor are other steps.

Those skilled in the art will recognize that the present invention may be manifested in a variety of forms other than the specific embodiments described and contemplated herein. Departures in form and detail may be made without departing from the spirit and scope of the invention. Accordingly, the invention should only be limited by the Claims included below.

The invention claimed is:

1. A method for processing near-infrared tissue measurements to provide a calibration model for noninvasive estimation of a biological parameter, comprising the steps of:
   noninvasively collecting a set of spectra with an analyzer;
   removing gross outliers from said spectra to yield outlier removed spectra;
   processing said outlier removed spectra to yield enhanced spectra;
   removing background interference from said enhanced spectra to yield background corrected spectra; and
   generating a calibration model using said background corrected spectra,
   wherein said step of processing comprises the step of:
       filtering said spectra with any of:
           an infinite-impulse response filter; and
           a finite-impulse response filter
       wherein said step of filtering comprises use of any of:
           a low-pass filter; and
           a high-pass filter, and
       wherein said high-pass filter comprises a break frequency determined via any of:
           a harmonic analysis of net analysis signal; and
           empirically through an exemplary set of data.

2. The method of claim 1 wherein said step of removing gross outliers comprises the steps of detecting and removing spectra having any of:
   instrument errors; and
   sampling errors.

3. The method of claim 2, wherein said instrument errors are detected based upon performance specifications comprising any of:
   noise;
   signal level;
   wavelength accuracy;
   wavelength precision;
   stray light; and
   measurement stability.

4. The method of claim 2, wherein said sampling errors are detected based upon any of:
   imprecision;
   tissue transients;
   tissue distortion; and
   poor surface contact.

5. The method of claim 1, wherein said step of filtering is optimized using a net analyte signal of said biological parameter.

6. The method of claim 1, wherein said low-pass filter maximizes a ratio of net analyte signal of said biological parameter to noise.

7. The method of claim 6, wherein said biological parameter comprises glucose concentration.

8. The method of claim 1, wherein said step of processing further comprises the step of:
   correcting said spectra using at least one of:
       a net analyte signal of said biological parameter;
       a scaling factor; and
       an offset correction.

9. The method of claim 8, wherein said step of filtering precedes said step of correcting.

10. The method of claim 9, wherein said step of processing further comprises a step of wavelength selection.

11. The method of claim 10, wherein said step of removing background interference comprises removal of any of:
    a spectral background; and
    a tissue template; and
    a mean of a data cluster.

12. The method of claim 1, wherein said step of removing background interference comprises removal of a tissue template.

13. The method of claim 1, further comprising the step of:
    performing enhanced outlier detection and removal of outlier spectra on said background corrected spectra to yield processed spectra.

14. The method of claim 13, wherein said step of performing enhanced outlier detection comprises the step of:
    comparing said background corrected spectra to a specification through any of:
        a distance measurement;
        a cluster analysis; and
        a principal component analysis.

* * * * *